United States Patent [19]

Miller et al.

[11] Patent Number: 4,804,500

[45] Date of Patent: Feb. 14, 1989

[54] AMINE DEALKYLATION PROCESS

[75] Inventors: William H. Miller, Glendale; Terry M. Balthazor, St. Louis, both of Mo.

[73] Assignee: Monsanto Company, St. Louis, Mo.

[21] Appl. No.: 841,149

[22] Filed: Mar. 19, 1986

Related U.S. Application Data

[63] Continuation-in-part of Ser. No. 725,856, Apr. 22, 1985, abandoned.

[51] Int. Cl.$^4$ .................. C07F 9/38; C07C 101/06; C07C 101.12
[52] U.S. Cl. .................. 260/502.5 E; 260/502.5 F; 562/571; 562/575
[58] Field of Search .................. 562/571, 575; 260/502.5 E, 502.5 F

[56] References Cited

U.S. PATENT DOCUMENTS

| | | | |
|---|---|---|---|
| 2,384,816 | 9/1945 | Curme et al. | 562/526 |
| 2,384,817 | 9/1945 | Chitwood | 562/526 |
| 3,835,000 | 9/1974 | Frazier et al. | 204/78 |
| 3,842,081 | 10/1974 | Schulze et al. | 562/418 |
| 4,442,041 | 4/1984 | Subramanian | 260/502.5 F |

*Primary Examiner*—J. E. Evans
*Attorney, Agent, or Firm*—Frank D. Shearin

[57] ABSTRACT

Amino acids can be produced from suitable tertiary and secondary amines by dealkylation using an alkali metal hydroxide.

9 Claims, No Drawings

AMINE DEALKYLATION PROCESS

CROSS REFERENCES TO RELATED APPLICATIONS

This application is a Continuation-in-Part of application Ser. No. 725,856, filed Apr. 22, 1985 and now abandoned.

BACKGROUND OF THE INVENTION

The present invention relates to a process for dealkylating a substituted amine and is useful in the preparation of a wide variety of amine-containing chemicals.

In the synthesis of many useful chemical compounds comprising amine groups, it is sometimes necessary to protect the amine group from reaction with another functional group in the molecule, or from reaction with a chemical effecting modification of another part of the molecule. This can often be done by preparing a derivative of the amine group from which the original amine group may readily be regenerated. Protection of an amine group in this way has in the past been done by formation of carbamates, amides, imines, enamines and N-hetero atom derivatives.

Another method of amine group protection that is particularly relevant to the present invention is the use of an alkyl group. However, the essence of protection is that the group can be readily removed. While aralkyl groups with the aryl group α to the nitrogen can be removed by reductive processes, it has been the view that alkyl groups need to contain another functional group to facilitate cleavage of the N-C bond. This subject is fully discussed in "Protective Groups in Organic Synthesis" by T. W. Greene (Wiley & Sons, 1981). Amino group protection is discussed in Chapter 7.

Protection of a primary or secondary amine group using an alkyl group is usually very effective since the alkyl group is, generally speaking, quite inactive in most organic reactions. It is, however, quite difficult to remove for essentially the same reason.

The study of the carbon/nitrogen bond of amines has been the subject of study in recent years. For example, Murahashi and Watanabe disclosed the transition metal catalyzed hydrolysis of tertiary amines with water in an article entitled "Palladium Catalyzed Hydrolysis of Tertiary Amines With Water" published in the Journal of the American Chemical Society 101, 7429 (1979). In this publication it was reported that catalytic oxidation of tertiary amines in the absence of oxygen proceeded generally and efficiently with palladium catalysts to provide secondary amines and carbonyl compounds.

U.S. Pat. No. 4,442,041 to Subramanian discloses a process for preparing N-phosphonomethylglycine, a secondary amine, by reacting an alkali metal hydroxide with N-(diethylphosphonomethyl)iminobisethanol, a tertiary amine, in the presence of a zinc oxide or cadmium oxide catalyst, and thereafter acidifying the product formed.

Now, a process has been discovered by which substituted or unsubstituted alkyl groups can be removed from secondary or tertiary amines to yield the corresponding primary or secondary amine, respectively. The dealkylation process of the present invention is useful, not only in the context of the removal of an alkyl amine-protecting group, but also in the synthesis of selected primary or secondary amines in which the precursor compound is one containing an alkyl-substituted amine group. Another distinct advantage is the lack of requirement for a heavy metal catalyst in the reaction mixture, which eliminates the cost and handling of such a catalyst, and also the problems associated with contamination of the product and waste streams by said heavy metal catalyst.

SUMMARY OF THE INVENTION

These and other advantages are achieved by a dealkylation process for the production of primary or secondary amines which comprises reacting, in the absence of zinc oxide or cadmium oxide, at a temperature from 250° C. to 400° C., an amine having the formula:

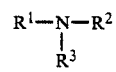

wherein $R^1$ is selected from groups containing an acid function promoting solubility of the amine in aqueous alkaline solution and containing at least one acidic —OH group; $R^2$ is hydrogen, methyl, benzyl, $R^1$ or $R^3$ provided that if either of $R^1$ and $R^2$ is —CH$_2$COOH the other may not be —CH$_2$PO$_3$H$_2$; and $R^3$ is selected from groups having the formula:

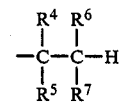

wherein $R^4$, $R^5$ are each individually hydrogen, $C_1$–$C_6$ alkyl, aryl or substituted aryl; $R^6$ and $R^7$ are, independently selected from, $R^4$, $R^5$, hydroxy, $C_1$–$C_6$ alkoxy, aryloxy, halogen, —SH, $C_1$–$C_6$ thioalkyl, —NHR$^8$, and —NR$^8{}_2$ (where each $R^8$ is a $C_1$ to $C_6$ alkyl group) or, where $R^6$ is H, $R^7$ can be a group with the formula: —NR$^1$R$^2$; or $R^3$ and $R^2$ together with the nitrogen can form a heterocyclic group; with an alkali in aqueous solution in at least the stoichiometric amount of alkali needed to neutralize any acid groups present in the amine, so as to produce a compound in which the $R^3$ group has been replaced by hydrogen.

DESCRIPTION OF THE INVENTION

The reaction according to the invention can be represented diagrammatically as follows:

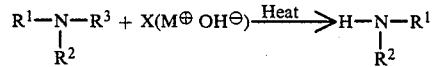

where M is an alkali metal and X is at least the number of free acid groups in the amine so as to ensure that the reaction occurs in alkaline solution. Usually from 1 to 6 moles of alkali for each acidic group in the amine are used. In preferred reactions this ratio is from 3:2 to 3:1.

The group $R^3$ is essentially an alkyl group containing at least one hydrogen on the β carbon atom. The group may, if desired, be substituted by the various groups specified above. These are groups that do not interfere with, or generate competing reactions to, the dealkylation process of the invention. The group split off ($R^3$) is usually released in the form of an alkene. In the case of the simplest $R^3$ groups such as ethyl, propyl and isopropyl, the alkenes formed are gases, and thus cause no separation problems during product isolation.

Since the reaction takes place in aqueous solution, it is essential that at least one of the groups $R^1$ or $R^2$ in the reaction material provides acidic —OH groups or acid derivatives that either themselves render the amine water soluble, or produce a water soluble derivative in the presence of the alkali reactant. Suitable groups that can be represented by $R^1$ include, for example:

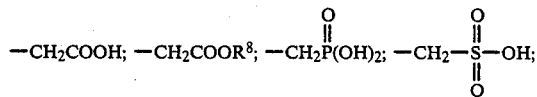

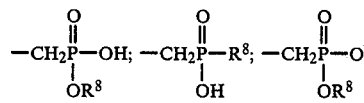

The reaction temperature is between 250° C. and 400° C., and since the reaction occurs in aqueous solution, an autoclave capable of withstanding the autogenous pressures generated by the aqueous reaction mixtures at these temperatures must be used.

The alkali most commonly used is sodium hydroxide but potassium hydroxide can also be used. The other alkali metal hydroxides can be used but are not generally preferred either because of cost or general effectiveness.

The use of zinc oxide or cadmium oxide catalysts of U.S. Pat. No. 4,442,041 is not contemplated in the process of the present invention. Although Applicants do not wish to be bound by any particular theory, it has been shown that the reactants are sufficiently active under the present process conditions that a zinc oxide or cadmium oxide catalyst is unnecessary, and, in fact, the presence of such catalysts has been shown to be detrimental. Elimination of any catalysts avoids the cost and handling of a catalyst, and the problems associated with contamination of the desired product and waste streams by the catalyst.

DESCRIPTION OF PREFERRED EMBODIMENTS

The process of the invention is particularly useful for the preparation of amino acids from their N-alkyl derivatives. Particularly valuable amino acids (because of their utility as intermediates in the production of a range of agricultural and pharmaceutical chemicals) include glycine, sarcosine and iminodiacetic acid (IDA).

The following chart gives the results of a number of reactions according to the invention resulting in the production of the amino acid indicated. In each case the reaction temperature was 300° C. and the alkali was sodium hydroxide. The reactions are generically represented by the formula:

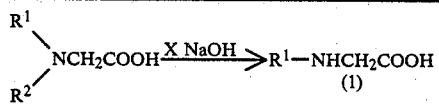

| $R_1$ | $R_2$ | X | Time (hours) | Yield % |
|---|---|---|---|---|
| $CH_3$— | $(CH_3)_2CH$— | 2 | 6 | 50–70 |
| H— | $(CH_3)_2CH$— | 2 | 6 | 8 |
| $HOOCCH_2$— | $HOCH_2CH_2$— | 3 | 3 | 80 |
| $HOOCCH_2$— | $(CH_3)_2CH$— | 3 | 3 | 64 |

-continued

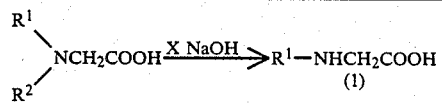

| $R_1$ | $R_2$ | X | Time (hours) | Yield % |
|---|---|---|---|---|
| $HOOCCH_2$— | $(HO_2CCH_2)_2NCH_2CH_2$— | 5 | 3 | 22 |

Another useful class of amines contains a phosphonic acid group such as aminomethylphosphonic acid (AMPA) and its derivatives. The following chart shows the production of AMPA using the process of the invention applied to various N-alkyl derivatives in the following reaction:

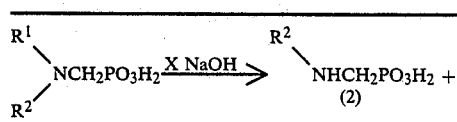

| $R^1$ | $R^2$ | X | Time (hours) | °C. | % (2) | % (3) |
|---|---|---|---|---|---|---|
| H— | $(CH_3)_2CH$— | 3 | 3H | 300 | 68 | 25 |
| $(CH_3)_2CH$— | $(CH_3)_2CH$— | 5 | 5H | 325 | 29 | 61 |
| $(CH_3)_2CH$— | $(CH_3)_2CH$— | 5 | 0.5 H | 325 | 91 | 8 |
| $CH_3CH_2$— | $CH_3CH_2$— | 5 | 5H | 325 | 2 | 77 |
| $CH_3CH_2$— | $CH_3CH_2$— | 10 | 5H | 325 | 12 | 70 |
| $CH_3CH_2$— | $CH_3CH_2$— | 4 | 10H | 325 | 2 | 72 |
| $CH_3CH_2$— | $CH_3CH_2$— | 3 | 5H | 325 | 39 | 52 |

Substrate, ($R^1 + R^2$) forms a heterocyclic ring.

| | | X | Time (hours) | °C. | % (2) | % (3) |
|---|---|---|---|---|---|---|
| | Y = H | 12 | 7H | 300 | — | 18 |
| | Y = $CH_3$ | 12 | 7H | 300 | — | 42 |

(piperazine structure with $PO_3H_2$–$CH_2$–N–Y and Y–N–$CH_2$–$PO_3H_2$)

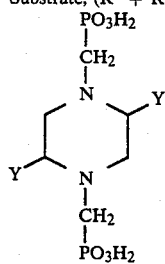

| | X | Time (hours) | °C. | % (2) | % (3) |
|---|---|---|---|---|---|
| | 5 | 5H | 325 | — | 37 |

It is observed that where more than one alkyl group is to be removed, better results are obtained by increasing the stoichiometric excess of base and increasing the overall dilution factor of the reaction mixture. In any event the second elimination is notably slower than the first. The information in the table also indicates that by adjusting the amount of caustic present and the reaction time, either mono- or di-dealkylation can be optimized.

The invention is further illustrated by, but not limited to, the following examples.

EXAMPLE 1

A 100 ml Monel autoclave was charged with 5.0 g (0.038 mol) of N-isopropyl-N-methylglycine, 6.0 g (0.076 mol) of 50% NaOH solution, and 9 ml of water to give a solution. The vessel was closed and the head space flushed for several minutes with $N_2$. The reactor was then sealed and heated to 300° C. over a one hour period. As a consequence of this temperature, an internal pressure of $6.1 \times 10^6$ N/M² had developed. While the reaction temperature was maintained at 300° C. for six hours, the pressure rose to $7.0 \times 10^6$ N/M² as a consequence of propene being liberated (confirmation of propene was obtained by mass spectral analysis of the head space gases). After the heating period, the reactor was cooled, excess pressure was released, and the reaction mixture was diluted with water. An analytical sample was examined by HPLC. which determined the yield of sarcosine to be 2.38 g (71%). The reaction mixture was neutralized by addition of 6.3 ml of concentrated HCl and purified by ion-exchange chromatography (Amberlite CG-50 resin) to yield 51% of the theoretical amount of sarcosine.

EXAMPLE 2

A 100 ml Monel autoclave was charged with 4.27 g (24.4 mmol) of N-isopropyliminodiacetic acid, 5.8 g (73 mmol) of a 50% NaOH solution, and 12 ml of water to give a solution. The reactor was closed and the head space was flushed with $N_2$ before sealing the vessel and heating it to 300° C. When the vessel reached 300° C., an internal pressure of $5.82 \times 10^6$ N/M² had developed. During the three hour heating time at 300° C. the pressure rose to $6.31 \times 10^6$ N/M². When the reactor cooled, excess pressure was vented and the reaction mixture was neutralized with 73 mmol of HCl. A solution of the final product was analyzed by HPLC. and was determined to contain 2.07 g (64%) of iminodiacetic acid and 0.66 g (16%) of the starting substrate.

EXAMPLE 3

A 100 ml Monel autoclave was charged with 7.15 g (40.3 mmol) of N-(2-hydroxyethyl)iminodiacetic acid, 9.6 g (121 mmol) of a 50% NaOH solution, and 12 ml of water to give a solution. The head space of the reactor was flushed with $N_2$, sealed, and then the vessel was heated to 300° C. When the reactor reached this temperature an internal pressure of $5.82 \times 10^6$ N/M² had developed. During the course of heating at 300° C. for three hours, the pressure rose to $7.55 \times 10^6$ N/M². The reactor was allowed to cool, excess pressure was released, and the reaction mixture was diluted with 10 ml of water. The reaction was neutralized by the addition of 10 ml of concentrated HCl. HPLC of the final solution indicated a total of 4.31 g (80.4%) of iminodiacetic acid had been prepared.

EXAMPLE 4

To a 100 ml Monel autoclave was added 2.71 g (16.2 mmol) of N,N-diethylaminomethylphosphonic acid 6.45 g (81 mmol) of a 50% NaOH solution, and 10 ml of water to give a solution. The head space of the reactor was flushed with $N_2$ for several minutes. The reactor was then sealed and heated to 325° C. over the course of an hour. At this temperature an internal pressure of $4.65 \times 10^6$ N/M² had developed. The reaction was maintained at 300° C. for five hours during which time the pressure in the vessel increased to approximately $7.69 \times 10^6$ N/M². After cooling the vessel and releasing excess pressure, the reaction mixture was diluted with 10 ml of water, neutralized with 6.6 ml of concentrated HCl, and evaporated to dryness. This residue was taken up in concentrated HCl and NaCl was filtered off. The filtrate was evaporated to leave an oil which was purified by ion-exchange chromatography (Dowex 50x8-400). Only one major peak was isolated (1.43 g). By NMR this was determined to consist of 1.38 g (76.6%) of aminomethylphosphonic acid and 0.05 g (2.2%) of N-ethylaminomethylphosphonic acid.

EXAMPLE 5

To a 100 ml Monel autoclave was added 3.16 g (16.2 mmol) of N,N-diisopropylaminomethylphosphonic acid, 6.48 g (81 mmol) of a 50% NaOH solution, and 10 ml of water to give a solution. The head space of the vessel was flushed with $N_2$ for several minutes and then the reactor was sealed. The vessel was heated to 325° C. over the course of 50 minutes and held at that temperature for only 25 additional minutes. During the period at 325° C. the internal pressure of the reactor rose from $6.58 \times 10^6$ to $6.80 \times 10^6$ N/M². The system was allowed to cool, excess pressure was released, and the reaction mixture was diluted with water. The solution was neutralized with 6.7 ml of concentrated HCl and evaporated to dryness. The residue was taken up in concentrated HCl and NaCl was filtered off. The filtrate was evaporated to an oil and purified by ion-exchange chromatography (Dowex 50×8-400) to give only one major peak (2.4 g). By NMR this material was determined to consist of 2.25 g (90.6%) of N-isopropylaminomethylphosphonic acid and 0.15 g (8.4%) of aminomethylphosphonic acid.

The amino acids produced by the process of the invention are useful intermediates in the production of a wide range of chemicals with therapeutic or phytotoxic applications.

For example both iminodiacetic acid and aminomethylphosphonic acid can each be used as a starting material (in different processes of course) for the production of N-phosphonomethylglycine, the active ingredient in an extremely effective systemic contact herbicide.

What is claimed is

1. A dealkylation process for the production of primary and secondary amines which comprises reacting, in the absence of zinc oxide or cadmium oxide, at a temperature of from 250° C. to 400° C., an amine having the formula:

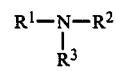

wherein $R^1$ is selected from groups containing an acidic function promoting solubility of the amine in aqueous alkaline solution and containing at least one acidic —OH group; $R^2$ is hydrogen, methyl, benzyl, $R^1$ or $R^3$, provided that if either of $R^1$ and $R^2$ is —CH₂COOH the other may not be —CH₂PO₃H₂; and $R^3$ is selected from groups having the formula:

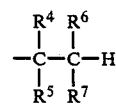

wherein $R^4$ and $R^5$ are each individually hydrogen, $C_1$–$C_6$ alkyl, aryl or substituted aryl, $R^6$ and $R^7$ are independently selected from $R^4$, $R^5$, $C_1$–$C_6$ alkoxy, aryloxy, halogen, $C_1$–$C_6$ thioalkyl, —NHR⁸, NR⁸₂ (where $R^8$ is a $C_1$–$C_6$ alkyl group) or, where $R^6$ is H, $R^7$ can be a group with the formula: —N(CH₂COOH)₂; or $R^3$ and $R^2$ together with the nitrogen can form a heterocylic group;

with an aqueous alkali in at least the stoichiometric amount of alkali needed to neutralize the acidic —OH groups, so as to produce a compound in which the group $R^3$ has been replaced by hydrogen.

2. A process according to claim 1 in which the alkali is sodium hydroxide.

3. A process according to claim 2 in which the ratio of moles of alkali per acidic group in the amine is from 1:1 to 6:1.

4. A process according to claim 1 in which the temperature is from 300° C.–400° C.

5. A process according to claim 1 in which $R^3$ is a $C_2$–$C_6$ alkyl group.

6. A process according to claim 1 in which $R^1$ is selected from —$CH_2COOH$ and —$CH_2PO_3H_2$.

7. A process according to claim 6 in which $R^1$ is —$CH_2PO_3H_2$ and $R^2$ is $R^3$ or H.

8. A process according to claim 6 in which $R^1$ is —$CH_2COOH$ and $R^2$ is $R^3$ or H.

9. A process according to claim 6 in which $R^3$ is a $C_2$–$C_6$ alkyl group and amine is heated at 300° C. to 400° C. in the presence of aqueous sodium hydroxide.

* * * * *